US011800977B2

(12) United States Patent
Verdooner et al.

(10) Patent No.: US 11,800,977 B2
(45) Date of Patent: Oct. 31, 2023

(54) APPARATUS AND METHOD FOR SELF-ADMINISTRATION OF OPTICAL SCANNING OF A PERSON'S EYE OPTICAL SYSTEM

(71) Applicant: OCTHealth, LLC, Sacramento, CA (US)

(72) Inventors: Steven Verdooner, Sacramento, CA (US); John Rogers, Canterbury (GB)

(73) Assignee: OCTHealth, LLC, Sacramento, CA (US)

( * ) Notice: Subject to any disclaimer, the term of this patent is extended or adjusted under 35 U.S.C. 154(b) by 467 days.

(21) Appl. No.: 16/177,004

(22) Filed: Oct. 31, 2018

(65) Prior Publication Data
US 2019/0133441 A1     May 9, 2019

Related U.S. Application Data

(60) Provisional application No. 62/579,599, filed on Oct. 31, 2017.

(51) Int. Cl.
*A61B 3/14*      (2006.01)
*A61B 3/10*      (2006.01)
(Continued)

(52) U.S. Cl.
CPC .............. *A61B 3/14* (2013.01); *A61B 3/0008* (2013.01); *A61B 3/028* (2013.01); *A61B 3/102* (2013.01); *A61B 3/12* (2013.01); *A61B 3/125* (2013.01)

(58) Field of Classification Search
CPC ........... A61B 3/14; A61B 3/028; A61B 3/102; A61B 3/0008; A61B 3/117–1176;
(Continued)

(56) References Cited

U.S. PATENT DOCUMENTS 9,772,497 B1    9/2017  Hewlitt et al.
10,285,582 B1*  5/2019  Kavusi ..................... A61B 3/14
(Continued)

FOREIGN PATENT DOCUMENTS

EP       2312994 A2      4/2011
WO    2010117386 A1     10/2010

OTHER PUBLICATIONS

International Search Report and the Written Opinion of the International Searching Authority, PCT/US18/58517, dated Apr. 24, 2019.

(Continued)

*Primary Examiner* — Collin X Beatty
(74) *Attorney, Agent, or Firm* — Lucas & Mercanti, LLP

(57) ABSTRACT

A system for obtaining optical coherence tomography of the optical system of a person, comprising: an eyepiece customized for alignment and positioning to contact a person's eye socket and having a lens pocket for receiving a refractive lens customized for the person's eye refraction characteristics; a condensing system for receiving light from the eyepiece; a scanning module optically connected to the condensing system and having a mirror tiltable in two directions for obtaining optical scanning data from the person's optical system; and a spectrometer and camera module optically connected to the scanning module for obtaining and storing the optical scanning data, wherein the eyepiece, condensing system and scanning module are arranged to provide an optical path for delivering a light beam to the person's eye, and receive reflected light to be directed to the scanning module.

31 Claims, 9 Drawing Sheets

(51) Int. Cl.
    *A61B 3/12*         (2006.01)
    *A61B 3/00*         (2006.01)
    *A61B 3/028*       (2006.01)
    *A61B 3/125*       (2006.01)

(58) Field of Classification Search
    CPC ............ A61B 3/12–125; A61B 3/1005; A61B 3/1025; A61B 3/107; A61F 9/009
    USPC .................................................. 351/205–221
    See application file for complete search history.

(56) References Cited

U.S. PATENT DOCUMENTS

| | | | |
|---|---|---|---|
| 2011/0299034 A1* | 12/2011 | Walsh | A61B 3/18 351/206 |
| 2014/0176904 A1* | 6/2014 | Lai | A61B 3/1035 351/206 |
| 2016/0157716 A1 | 6/2016 | Pamplona et al. | |
| 2016/0205298 A1 | 7/2016 | Zhou | |
| 2017/0150897 A1* | 6/2017 | Komaki | A61B 3/113 |
| 2018/0088310 A1* | 3/2018 | Hewlett | G02B 21/20 |
| 2018/0279870 A1* | 10/2018 | Walsh | A61B 3/10 |

OTHER PUBLICATIONS

Extended European Search Report, European Patent Application No. 18874891.7, based on PCT/US2018058517, dated Jun. 23, 2021.

\* cited by examiner

APPARATUS AND METHOD FOR SELF-ADMINISTRATION OF OPTICAL SCANNING OF A PERSON'S EYE OPTICAL SYSTEM

CROSS-REFERENCE TO RELATED APPLICATION

This application claims priority to U.S. Ser. No. 62/579,599, filed Oct. 31, 2017, which is incorporated by reference herein.

TECHNICAL FIELD

The present invention relates to an apparatus and method for a patient user to obtain optical scanning data of his eye optical system without an eye care professional.

BACKGROUND OF THE INVENTION

Optical Coherence Tomography (OCT) has become a standard of care in eye care practices for a variety of disorders that manifest in the retina. These devices range in price from $30,000 to $90,000 and typically require a skilled operator to obtain the desired results. More recently there are OCT devices that have the ability to automatically align to a patient's eye and to focus, but still require operator input and patient positioning. While these devices are now found in many eye care practices, they still require patients to visit the office for initial diagnosis and monitoring of disease progression. Patients are often sent away for months at a time, and occasionally have sudden changes in vision. These situations are potentially avoidable if there was greater access to devices, they were loser cost, and did not require and eye care professional operator to obtain scans.

SUMMARY OF THE INVENTION

The present invention solves this problem in multiple ways. First, the invention provides for significantly lower cost of goods utilizing a novel optical design that is customized to the patient. Presets for the device allow the device to be customized for the patient's eye refraction. In one embodiment their glasses prescription is utilized to manufacture a custom lens mounted in the eyepiece of the system for each of the patient's eyes. This aspect allows for a novel optical design and elimination of several moving parts that would normally be found in these other commercial devices that must accommodate a broad range of patient eye variance and facial topography composition. The primary use case that is contemplated is home use, whereby patients are able to self-align using a novel eyecup interface that contains a lens with the patient's refraction, mounted within the eyecup. Additional use cases include settings where a skilled operator and/or clinician may not be present. One example is a retail pharmacy clinic location, or embedding technology in a kiosk. The contours of the eyecup are novel with respect to protruding aspects that hold lids open and position to the orbit in a repeatable fashion. In the home use scenario, scans are performed without an operator and automatically uploaded to the cloud where image processing is performed to optimize scan quality, and layers segmented, measurements made, and measurements, data, and reports generated for review by an eye care or other medical professional. In one embodiment there is a subsystem that allows select measurements to be tracked over time in a dashboard view so as to track changes in measurements (like central retinal thickness, as one example). The eyecup may be disposable (single patient use) but can also be for repeated use, and cleaned between uses, and can include features that set machine information (such as the coherence position in OCT). In another embodiment the eyecup could be utilized in other ophthalmic measurement and imaging devices.

In summary, the invention solves the problem of ease-of-use for performing OCT measurements, for the prevention of vision loss between visits by having a low cost of goods thereby enabling potential rental of device. Cost reduction is achieved with multiple novel elements to be further described. Additionally, the cloud-based analysis aspect allows for a physicians to be immediately notified when there is a change that they wish to track and detect, and notify a patient to return to the practice for further evaluation and potential treatment.

While home use is the primary anticipated use case, in another embodiment the device could be located in other locations convenient to patients. In another embodiment the device could be mounted in a retail pharmacy kiosk or other kiosk that is utilized to collect biometric and other health information.

The invention differs from other inventions via the novel eyecup, novel eyecup containing lens customized to the patient, thereby allowing multiple moving parts to be eliminated and significant cost reduction and ease-of-use. This would allow a single hardware implementation of the device where all parameters are set using the customized eyecup. The customized eyecup and lens would allow correction of spherical and astigmatism errors either difficult or impossible with typical ophthalmic instruments and allow correction of higher order aberrations that are usually impossible with ophthalmic imaging instruments. The invention differs in light source and calibration method that allows for utilization of lower cost light source. The novelty of the use of a relatively inexpensive source and simple interferometer is not dependent on the eyecup or lens and could be used with any OCT system.

Primary improvements of the invention over other OCT devices are described above.

The process steps of using the invention may be as follows:

It is determined by the eye care professional that the diagnosis for a given patient warrants continuous home monitoring between visits so as to detect changes that may be occurring prior to loss of vision. One example use case would be tracking central retinal thickness over time as an early warning system.

The next step of the process is to obtain the patient's refraction and/or measure their glasses in a commercially available lens meter (per eye). This could also be achieved via tests more complex than an 'eye exam' or autorefractor measurement, (such as specialized OCT measurement of cornea and lens shapes and thicknesses), to give a more accurate measurement of optical correction needed to give the best possible retinal imaging.

Patients would then be tested with a test device to determine any other settings that need to be optimized for their given device, per eye.

Patients would be taught how to self-position on a device and would have several test measurements.

A customized eyecup would be manufactured per the patient's refraction (per eye). Said customized eyecup would contain the manufactured lens that matches their prescription.

A device would be shipped to their home along with the customized eyecup(s).

The device would be connected to home wifi or cellular internet for transmission of data.

Patients would self administer a test of obtain their OCT scan data.

Data would be automatically uploaded over the internet to the cloud for image processing, layer segmentation, analysis and reporting of results to an eye care professional.

Eye care professional would have a dashboard that displays results with color coding on those that are at risk per settings and thresholds of his choice.

Settings on the clinical viewer would be fully customizable in measurement views, analysis, thresholds for events, and automated contact of patient to come back to the office of the eye care professional for a visit (and other action items and messages for the patient that may or may not involve an office visit).

While the device could potentially be used to manage disease, the initial intended use for regulatory purposes it to be an early warning system to return for a visit to the office of the eye care professional, ahead of a regularly scheduled visit so as to prevent vision loss.

Uses of the invention would be for all diseases and disorders that manifest in the retina, not necessarily just retinal disease. In one embodiment the device could be used to monitor neurodegenerative diseases. The ways that the invention achieves the desired result is through its novel design that allows for both cost reduction, ease of use, self-administration, and automatically generated results.

DETAILED DESCRIPTION OF THE PREFERRED EMBODIMENTS

Figure 1A:
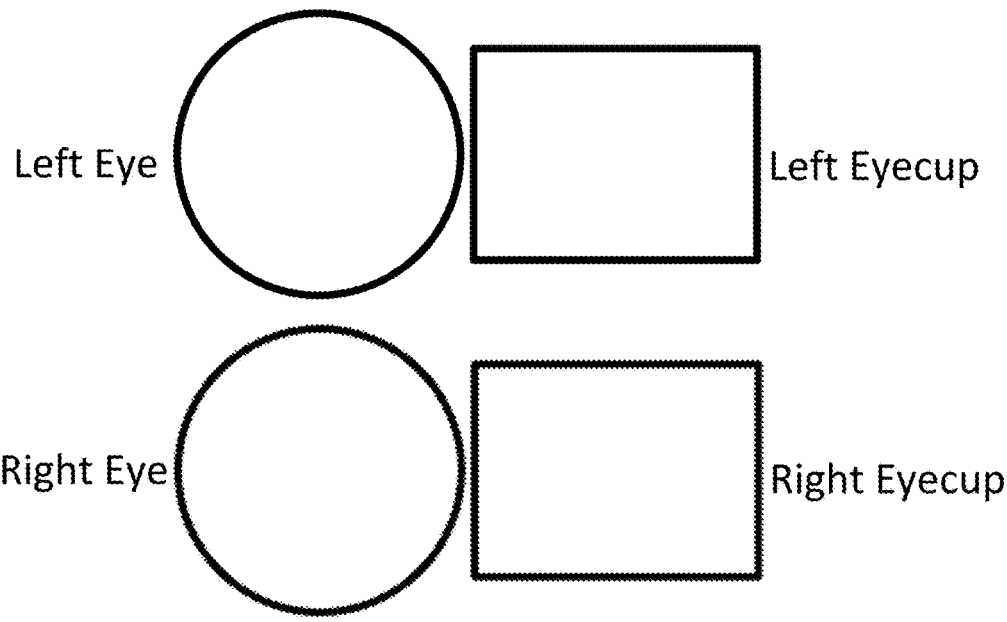
FIG. 1A is a block diagram of two eyes and two eyecups forming part of the invention.

A preferred embodiment will be described, but the invention will not be limited to this embodiment.

The invention provides an eyepiece for use in a system for obtaining data of the optical system of a person, comprising an eyepiece customized to contact and tightly fit in a person's eye socket and having a lens pocket for receiving a refractive lens customized for the person's eye refraction characteristics.

The eyepiece may further include a condensing system for receiving light from the eyepiece, a scanning module optically connected to the condensing system and having a mirror tiltable in two directions for obtaining optical scanning data from the person's optical system, an imaging system optically connected to the scanning module for obtaining and storing the optical scanning data, wherein the eyepiece, condensing system and scanning module are arranged to provide an optical path for delivering a light beam to the person's eye, and receive reflected light to be directed to the scanning module.

The eyepiece may further include a communication link for communicating the optical scanning data to a remote location for processing. The eyepiece and lens may be customized for any astigmatism and aberrations of the person, and may be customized for eye length of the person.

The eyepiece may include a right and left eyepiece for each of the right and left eyes of the person. The eyepiece may have right and left detachable eyecups each with an index and adapted to mate with a respective right and left eyepiece body to provide mating of the correct right or left eyecups with the respective eyepiece body.

The eyepiece lens pocket may be adapted to receive a lens of the person's prescription eyeglasses, or to contain a customized refractive lens for the person's eye.

The eyepiece may include an imaging beam generator which is adapted to transmit an imaging beam through the eyepiece, whereby the person's eye reflects a light beam back to the scanning module. The imaging beam generator may produce an infrared optical imaging beam.

The position between where the eyepiece contacts to the person's eye socket and the scanning module may be adjustable in length to adapt to the person's focusing eye length. The eyepiece may have a protrusion adapted to hold a person's eyelids open and position the eyepiece to the person's orbit.

The communication link may comprise the internet for communicating the optical scanning data to the cloud for image processing, analysis and access by an eye care professional.

The scanning module may be a MEMs scanning module. The eyepiece may further include a grid for a person to input any changes in vision. The grid may be an Amsler grid or Yannuzzi grid.

The eyepiece lens may be a variable lens or a phoropter trial lens set.

The eyepiece may contain an RFID chip to uniquely identify the person for whom the eyepiece is customized, and parameters for customization.

The eyepiece may include at least one filter. The eyepiece may include a lens optimized for imaging different areas of the retina of the person. The eyepiece may include a fundus imaging device, an eye measurement device, or an eyecup for performing a dry eye test. The eyepiece may include a customized eyecup having an electrical sensor for performing multifocal electrophysiology exams. The eyepiece may include a light source to illuminate an eye. The eyepiece may include an eyecup having a side which extends further to contact the side of a person's face. The eyepiece may include a wide-field imaging lens. The eyepiece may include a feedback loop to auto-capture imaging data of the eye. The eyepiece may be used in a system for obtaining optical coherence tomography.

The invention provides a system for obtaining data of the optical system of a person, comprising an eyepiece customized to contact and tightly fit in a person's eye socket and having a lens pocket for receiving a refractive lens customized for the person's eye refraction characteristics, a condensing system for receiving light from the eyepiece, a scanning module optically connected to the condensing system and having a mirror tiltable in two directions for obtaining optical scanning data from the person's optical system; and an imaging system optically connected to the scanning module for obtaining and storing the optical scanning data, wherein the eyepiece, condensing system and scanning module are arranged to provide an optical path for delivering a light beam to the person's eye, and receive reflected light to be directed to the scanning module.

Figure 1B:
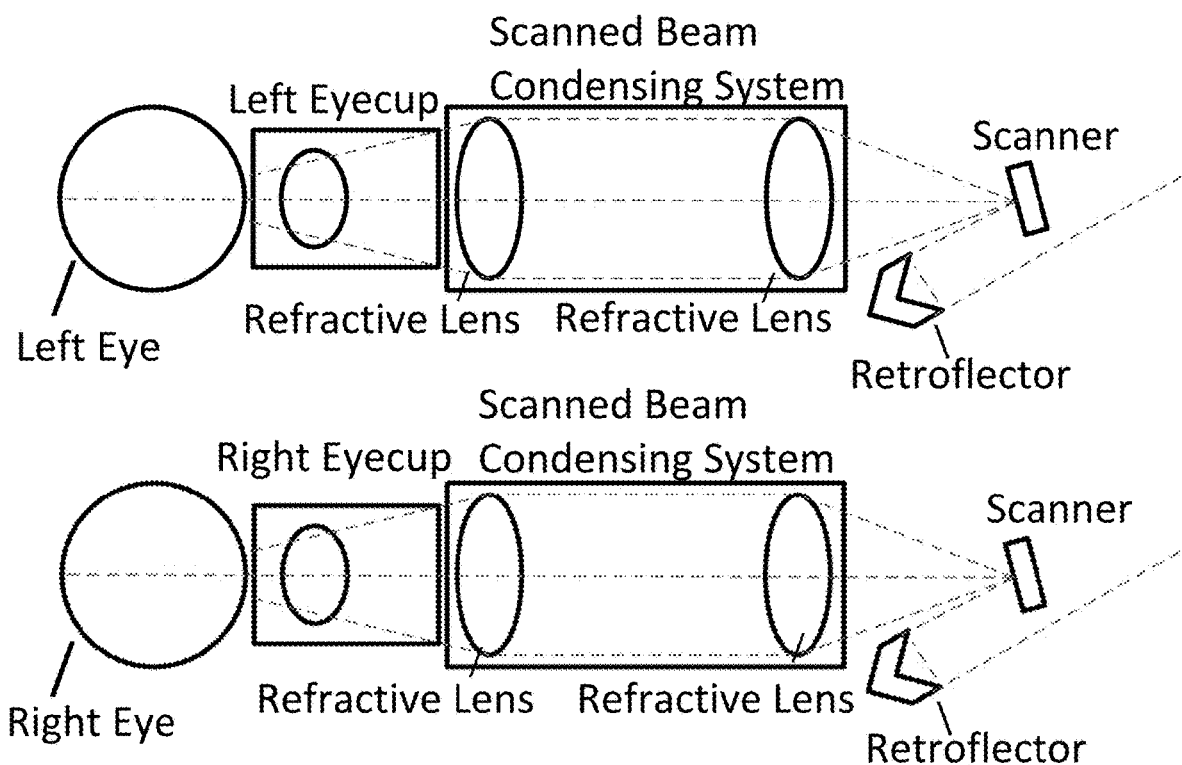
FIG. 1B is a block diagram of an eye, eyecup including refractive compensating element for the eye imaged, scanned beam condensing system MEMs (microelectro mechanical system) (or galvoscanner) and retro reflector, with beam traces in dotted lines.
Figure 1C:
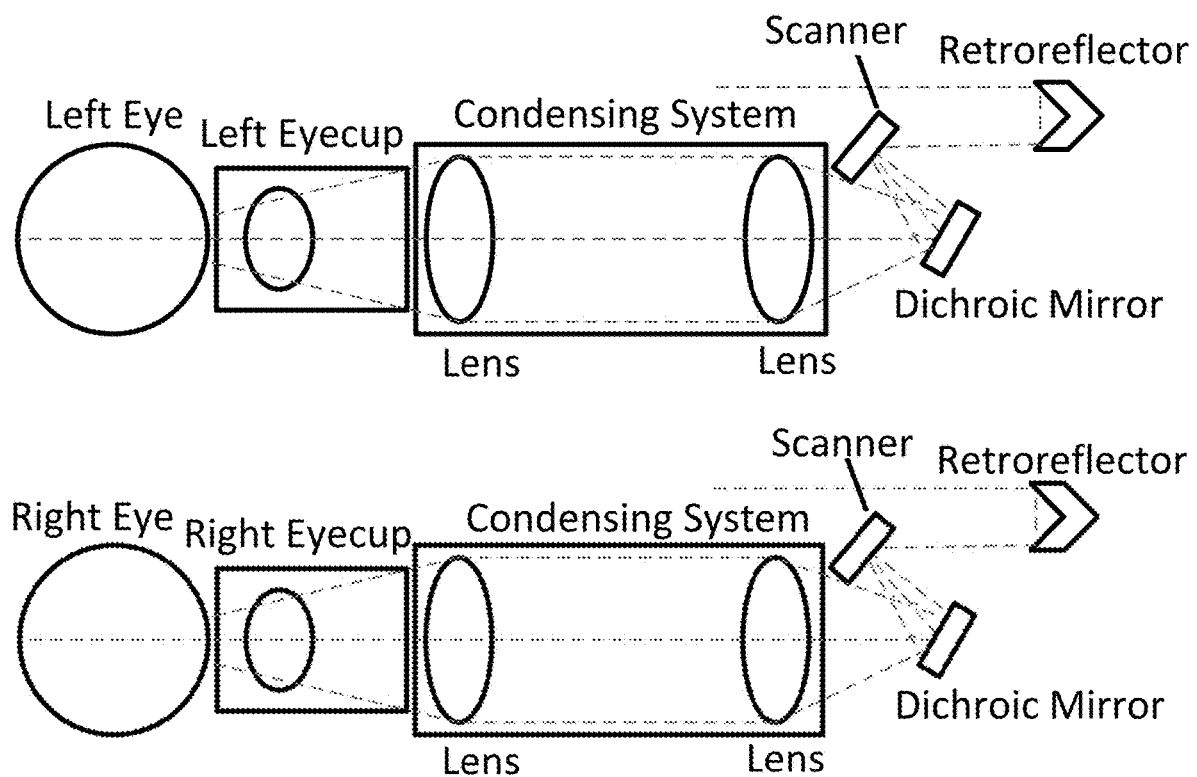
FIG. 1C is an alternative arrangement of FIG. 1B, with a dichroic mirror added.
Figure 2A:
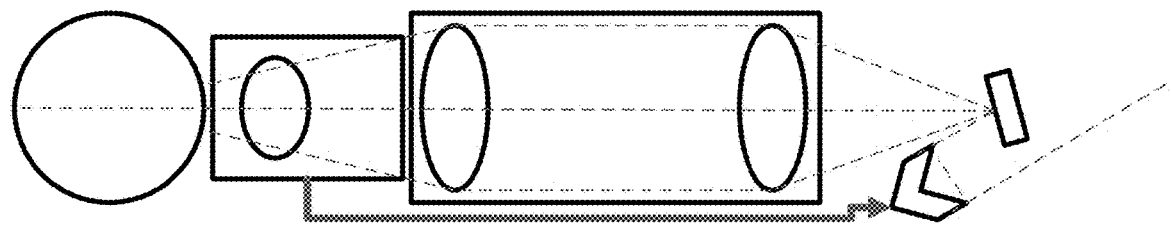
FIG. 2A is an alternative arrangement of FIG. 1B, having an adjustable length arm, where the optical path for one eye is longer, the arm length being customized for the eye being examined, the length determining the position of the retroreflector in the system. The length can be set by the rotation of a circular part that is inclined.
Figure 2A:
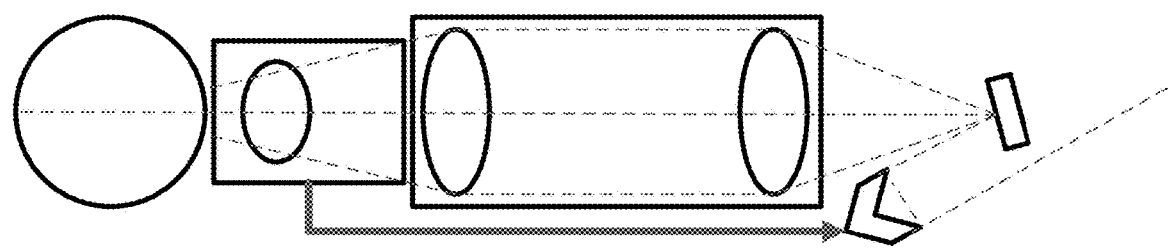
Figure 2B:
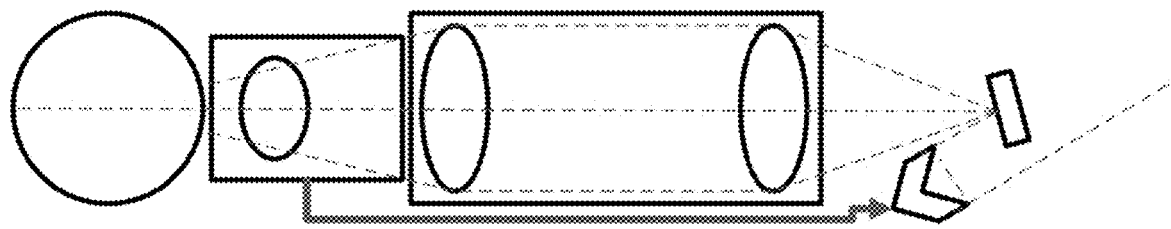
FIG. 2B is another alternative arrangement of FIG. 1B, like FIG. 2A, but where the optical path for the other eye is longer.
Figure 2B:
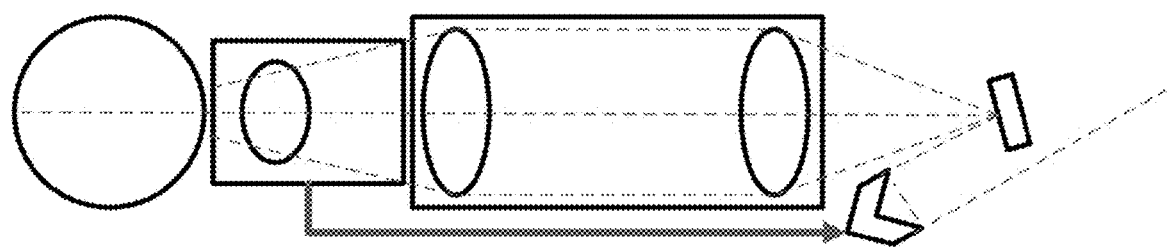
Figure 2C:
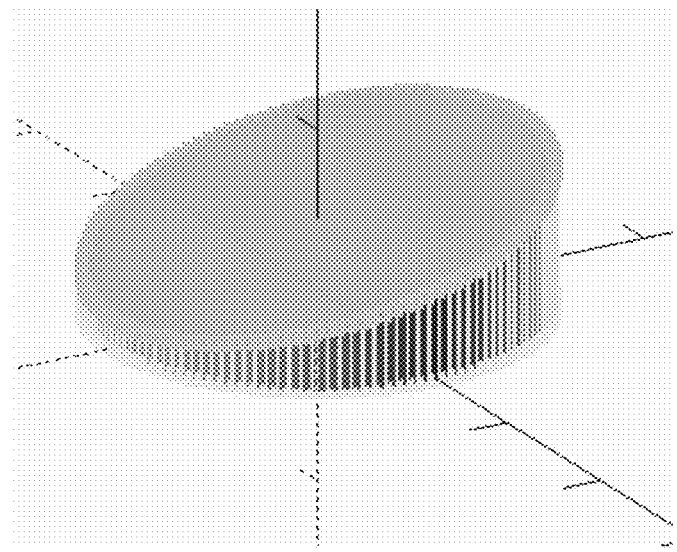
FIG. 2C shows a circular part usable in the embodiments of FIGS. 2A and 2B to adjust the length by rotating the circular part having an inclined face.
Figure 3:
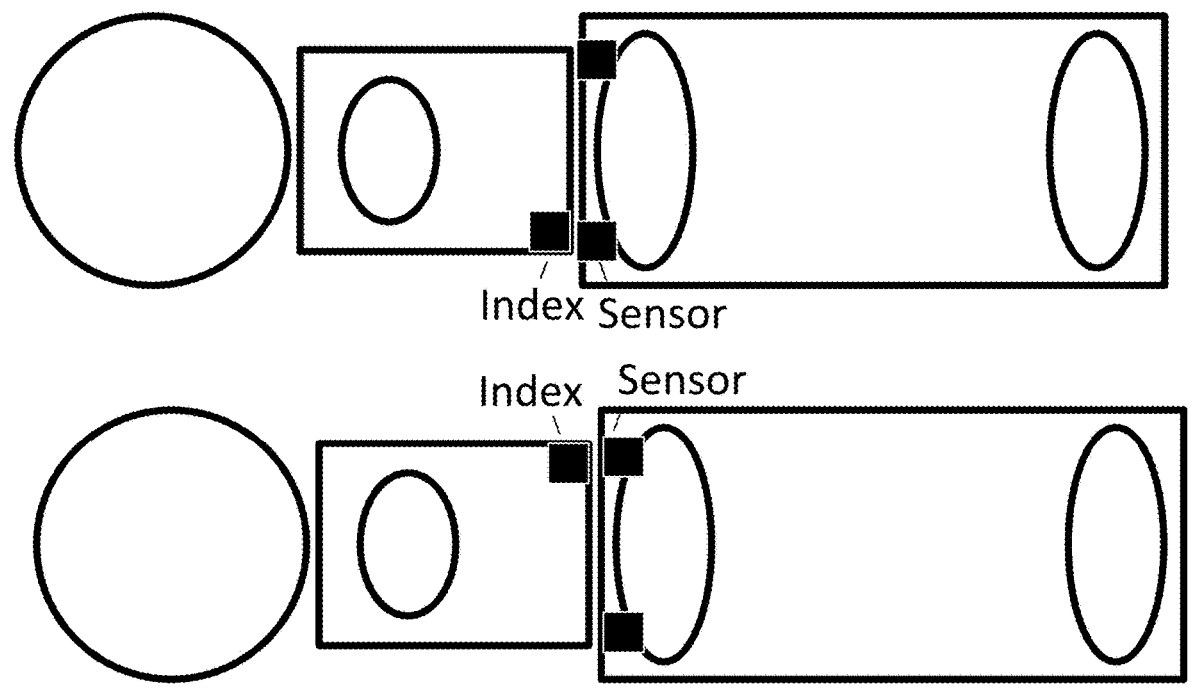
FIG. 3 is block diagram of a similar system of FIGS. 1A, 1B, 1C, 2A, 2B and 2C, wherein the eyecup contains indicia to indicate whether it is designed for the left eye or right eye. The relay lens of the condensing lens system contains a sensor to detect the indicia to know which sided eyecup is present. The sensor could be a mechanical switch in the relay lens system acted on by a protrusion on the eyecup.
Figure 4:
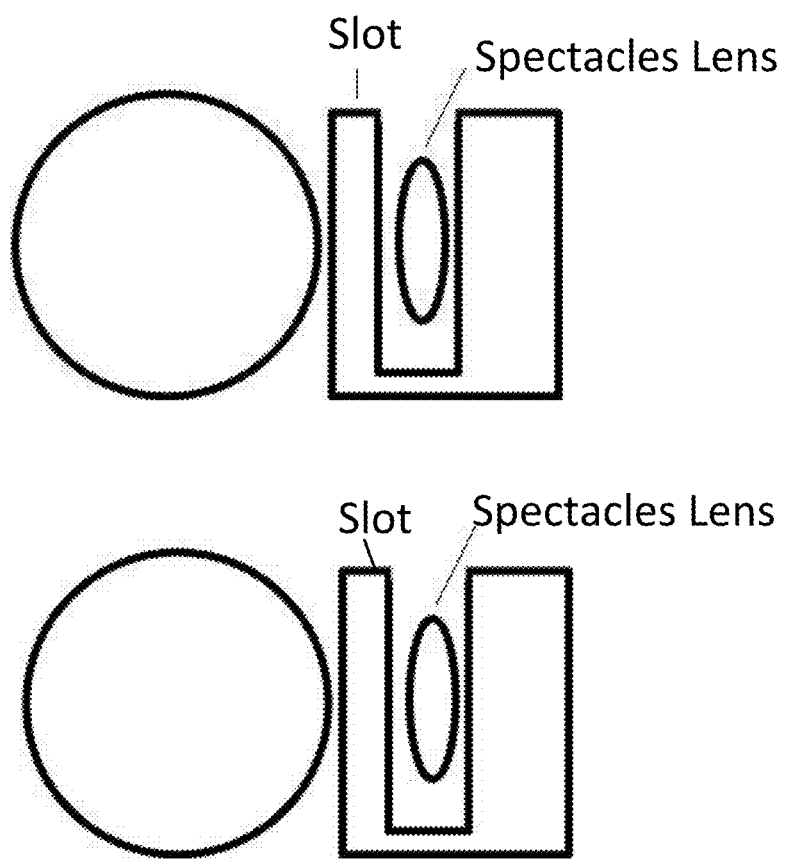
FIG. 4 shows an eyecup which contains a slot for receiving the user's eyeglasses or spectacles instead of having an embedded refractive compensating element, and the eyecup still provides a way to contact between the eye socket and the system to have the correct path length, with the user's eyeglasses providing the refractive correction.
Figure 5:
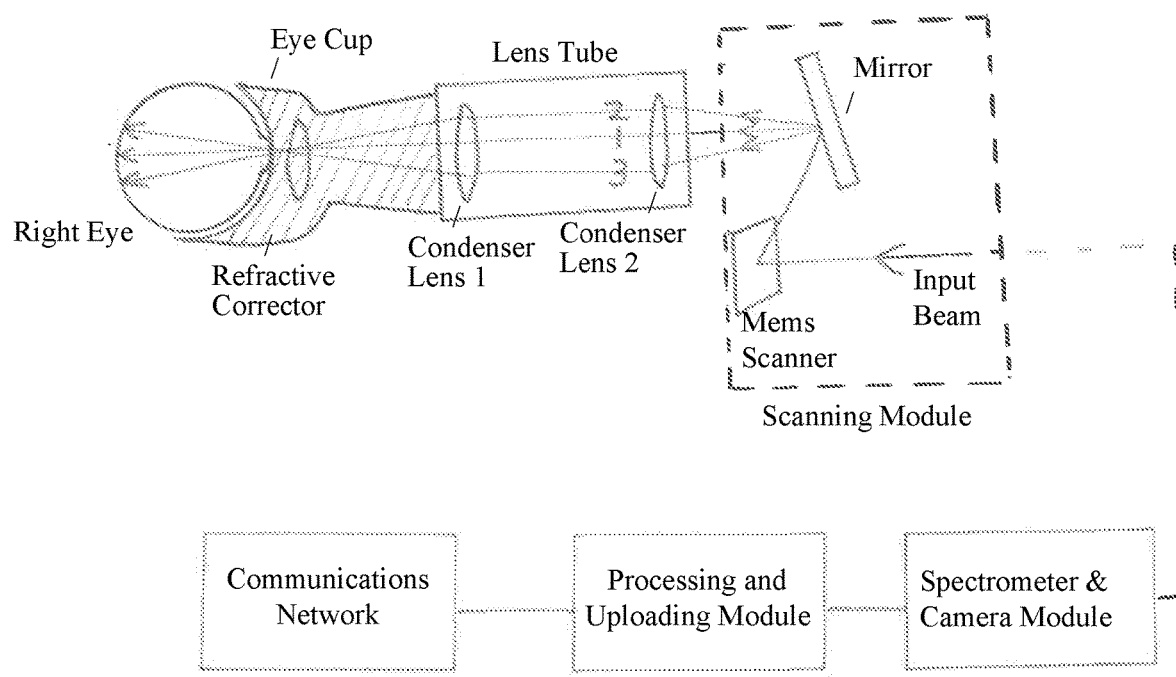
FIG. 5 is a block diagram showing a spectrometer and camera module, processing and uploading module and a communications network for transmitting the imaging data to a remote location such as the cloud for processing and access by an eye care professional. The eyecup shown is for a right eye and has a profile which extends around the side of a person's face to help in fitting and also identify the eyecup as a right eyecup. The left eyecup would be the mirror image of the right eyecup.
Figure 6A:
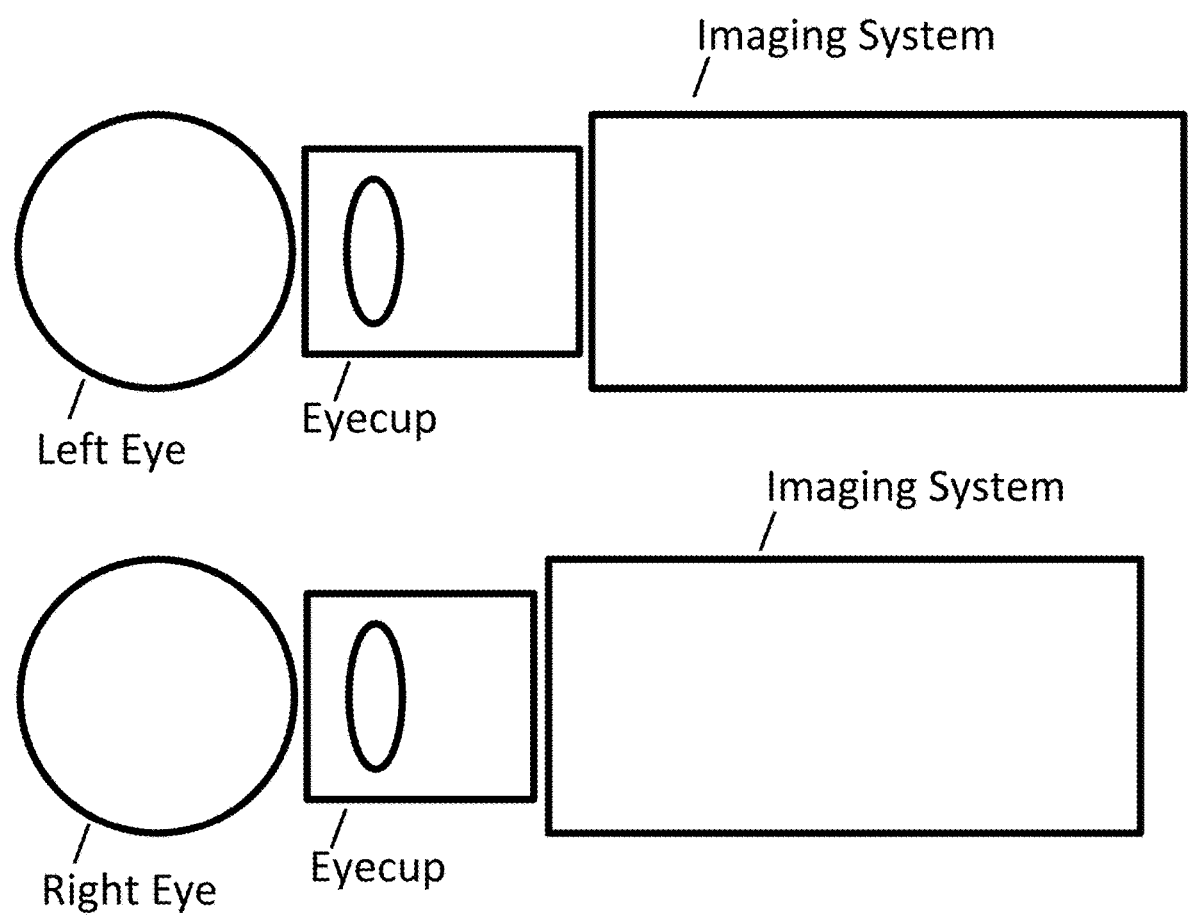
FIG. 6A shows in block form an eye, eyecup, and handheld or portable imaging system, wherein the eyecup abuts the eye and imaging system and sets the correct refraction and optical path length between the eye and imaging system so that the retina is at the correct distance from the system for the person. This is important for coherence based imaging techniques like OCT. This arrangement simplifies the operation and design of the imaging system and will reduce cost and complexity. In this Figure, the length of the eyecup for the left eye is longer than the length of the eyecup for the right eye.
Figure 6B:
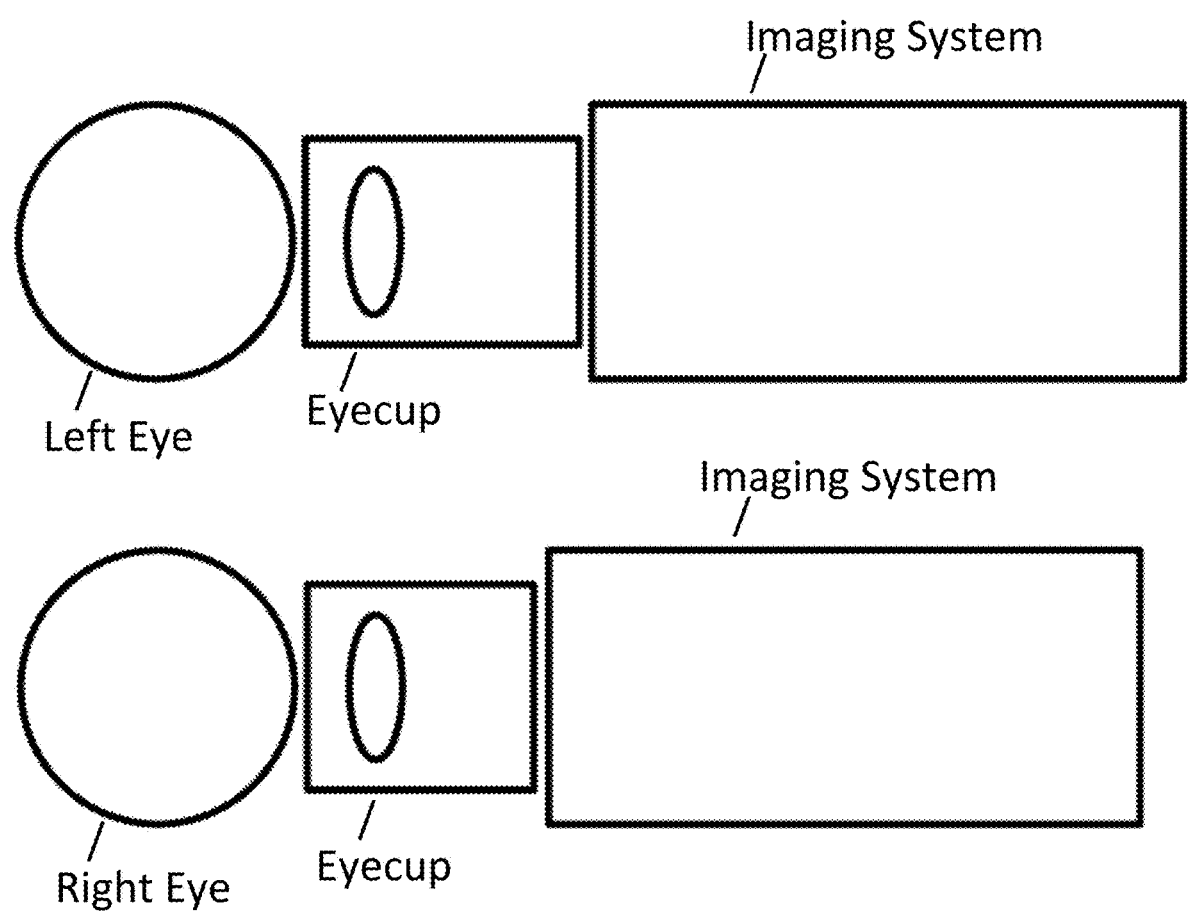
FIG. 6B shows a system like that in FIG. 6A, except that the length of the eyecup for the left eye is shorter than the length of the eyecup for the right eye. In each of the FIGS. 6A and 6B, the length of the eyecup is set based on the optical system of the person's eye.
Figure 7A:
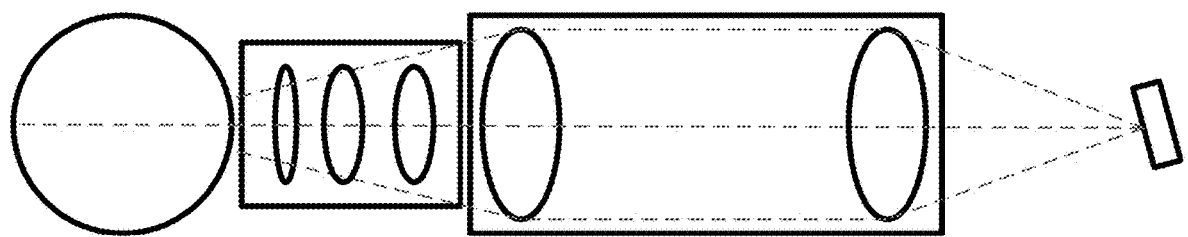
FIGS. 7A and 7B show in block from a system which contains a wide-angle relay lens system, wherein the eyecup contains, in addition to a refractive corrective lens, a lens system which increases the angle of view inside the eye.
Figure 7A:
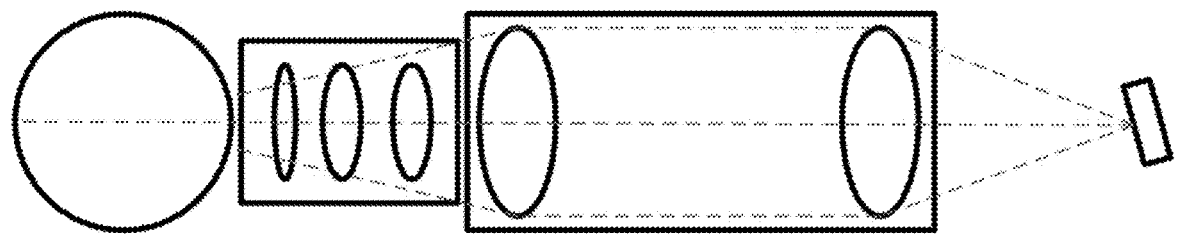
Figure 7B:
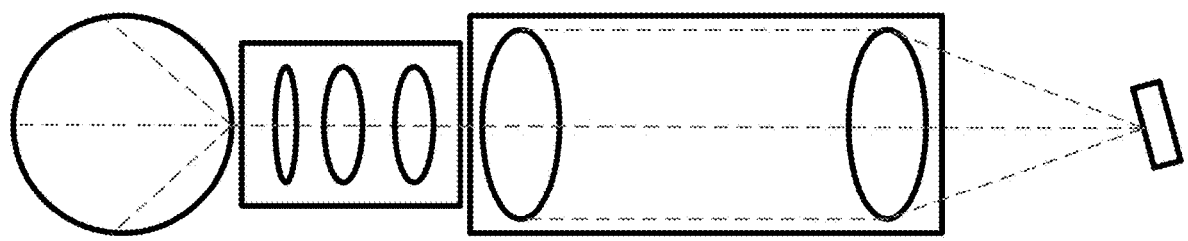
Figure 7B:
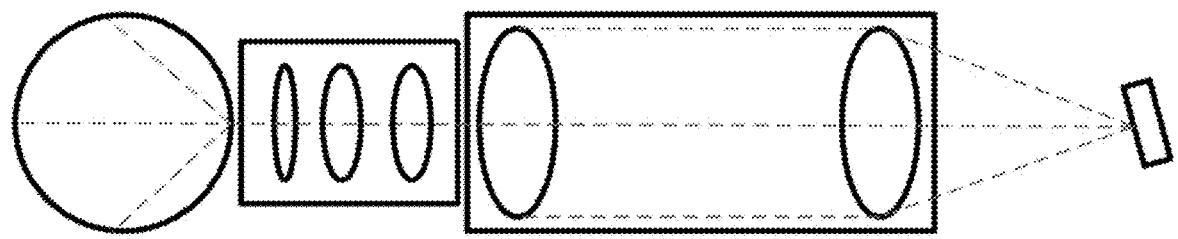

According to a preferred embodiment of the invention, FIG. 1 shows an eyecup module, containing novel design and elements that allow lids to be held open, while positioning to the ocular orbit, allowing repeatable positioning. The eyecup module also contains a lens, or multiple lenses that allow for customization to the patient's refraction including astigmatism and other aberrations. The eyecup also contains distance and other positioning settings so as to customize to a given patient's refraction.

Another part of the device is the micro electromechanical system (MEMS) scanning module. The module uses a single mirror that tilts in two directions (XY scanning) and allows for a more optimized optical arrangement. E.g. galvo scanners are typically made up of separate X and Y scanners. The novel combination with eyecup and other elements allows scanning of diverse patterns and regions, minimizing optical aberrations.

Another part of the device is the spectrometer and camera module. The novel combination with other elements allows for cost reduction and high quality. The broadband source and spectrometer of the proposed OCT system could be achieved with a swept source and receiver electronics with the required characteristics.

Another part of the device is the localized processing and uploading module for uploading images and data over the internet to the cloud. Processing could be completed in the cloud. In fact each scanning unit could be identical in hardware and software (eyecup contains customization) with all calibration files needed for processing being stored in the cloud.

Another part of the device is a grid (Amsler Grid, Yannuzzi Grid or other) that allows the user to also indicate via switch or audio voice detection that they have other changes due to metamorphopsia or other aspects that may cause a change in vision.

In an alternative embodiment, the device is a combination device that performs OCT as described, and also contains an Amsler Grid, contrast sensitivity, visual field, microperimetry or other functional vision assessment.

In an alternative embodiment the eyecup does not have a lens inserted but the customization is achieved in the device itself.

In an alternative embodiment a liquid lens or other variable lens setup is employed so as to customize to the patient's refraction.

In an alternative embodiment, a lens from a phoropter trial lens set is utilized to customize the patient's refraction.

In an alternative embodiment ophthalmic tests that typically take several minutes are performed over many days/months/years in several parts.

In an alternative embodiment, due to the novel optical design, the MEMS can be positioned in differing locations so as to optimize scan, field, target and viewing for other ancillary vision tests.

In an alternative embodiment the individual lens customization allows for post processing to be customized on an individual eye basis.

In an alternative embodiment, the coherence position is set per a pin or lever that is adjustable to varying lengths to create ideal position. This can be accomplished via a sliding mechanism, screw mechanism, or an angular surface that adjusts position to a keyed setting per eye when twisted. This keyed position per eye allows the device to know when each particular eye is being imaged. In another embodiment and optical switch is used to detect the right eye (OD) or left eye (OS) and know that the eye is properly positioned.

In an alternative embodiment an OCT feedback loop would determine optimal positioning and trigger scan capture and/or flag for presence of data and quality of data.

In an alternative embodiment an RFID chip is inserted into the eyecup to inform on test subject identification and parameters for device adjustment, and which eye is being imaged.

In an alternative embodiment, the MEMS allows for display of different patterns utilized in other vision and functional tests including but non limited to grids, Amsler Grid, Yannuzzi Grid, Adaptive Grids, contrast sensitivity, frequency doubled technology (FDT), visual acuity, perimetry, and micro-perimetry.

In an alternative embodiment, the device allows for an eyecup and optical channel for traditional (not OCT based) fundus imaging of various modalities.

In an alternative embodiment, the device allows for an eyecup and optical channel for traditional and other (not OCT based) ocular measurements of various modalities.

In an alternative embodiment spectral filters, single multiple, continuous can be mounted in the device and/or eyecup.

In an alternative embodiment one could modulate the super luminescent diode (SLD).

In an alternative embodiment, one could perform an eye tracking test for multiple disorders.

In an alternative embodiment one could incorporate a camera to perform pupilometry.

In an alternative embodiment one could incorporate lens autofluorescence and OCT technology for assessment of aggregated glycation end products for state of diabetes, and/or implied blood glucose/hemoglobin A1c levels.

In an alternative embodiment the eyecup is adaptable to multiple eye devices that allows for individual optimization per eye built into the eyecup and to add attenuation to the eyecup, and different filters on the eyecup.

In an alternative embodiment different sectors of the customized lens are optimized for imaging different areas of the retina. This could be achieved with a single optical element with the required shape, compound element or multi element assembly.

In an alternative embodiment, the eyepiece technology, including customized refraction per eye is incorporated into a device for traditional fundus imaging and wide field fundus imaging, thereby achieving decreased aberrations and better image quality in the central field and the periphery.

In an alternative embodiment the eyecup can be adapted for use on any eye imaging device to improve image quality including but not limited to fundus camera, OCT, slit lamp imaging device, smartphone imaging devices, widefield imaging devices (all in various modalities—color, OCT, red free, autofluorescence, fluorescein angiography, ICG angiography, hyperspectral, and multi-spectral imaging).

In an alternate embodiment the eyecup contains a lens system that allows for position of optical components close to the cornea to facilitate wide-field imaging In an alternative embodiment, the device with customized eyecup is utilized for a dry eye test.

In an alternative embodiment, the device is utilized for anterior segment and microscope mounted eye imaging applications.

In an alternative embodiment, the customized eyecup is used with on ophthalmic stimulus and/or imaging device for parts of a longer test conducted over several days. In this manner a longer test can be conducted in small portions over several consecutive days. This would mean that a test such as a visual 'perimetry test' or another previously described visual function test could be obtained in a 'distributed manner'.

In an alternative embodiment the customized eyecup contains an electrical sensor to perform multifocal electrophysiology exams.

In an alternative embodiment achievable source is used in the OCT system with a coherence length long enough so that no adjustments of coherence position is needed.

In an alternative embodiment a spectrometer design is used in the OCT system such that the imaging range is sufficient so that no adjustments of coherence position is needed.

In an alternative embodiment the optical beam waist at the cornea is sufficiently small so that no refractive element is needed.

In an alternative embodiment the eyecup with lens is customized to the patient is adapted to an existing or new device and optimized for use in other eye imaging devices (fundus cameras, Optos, OCT, etc.). This will correct aberrations specific to the patient.

In an alternative embodiment, illumination with a light source is built into the eyecup so as to illuminate trans-sceral for purposes of retinal imaging.

In an alternative embodiment, a wide field lens is fitted in the eyecup and then examined and/or imaged with an opthalmoscope, indirect ophthalmoscope, slit lamp, or other ophthalmic device.

In an alternative embodiment the eyecup is used to optimize positioning any handheld ophthalmic imaging and/or measurement device.

In an alternative embodiment the patient's own eyeglasses or spectacles are utilized in the optical train to correct for their own specific refraction and astigmatism.

In an alternative embodiment a wide field lens is mounted in the eyecup and either coupled or de-coupled from a retinal examination instrument (indirect or direct ophthalmoscope, slit lamp, smartphone-based imaging device) to image the retina.

The device may be used in a home environment, self-administered.

The device may be incorporated into a kiosk (like those found in retail pharmacies) for self-administration of test.

The device may be utilized in any setting where a skilled operator or medical professional is not present While a preferred embodiment with alternatives has been described, the invention is not limited to these embodiments, and its scope is defined only by way of the claims.

The invention claimed is:

1. An eyepiece for use in a system for obtaining data of the optical system of a person, comprising:
 an eyepiece customized to contact and tightly fit in a person's eye socket, wherein the eyepiece abuts the person's eye socket and an imaging system and sets the correct refraction and optical path length between the person's eye and imaging system so that the retina is at the correct distance from the imaging system for the person, and having a lens pocket having a refractive lens manufactured to be customized to match the person's eye refraction characteristics.

2. The eyepiece of claim 1, further including a condensing system for receiving light from the eyepiece.

3. The eyepiece of claim 2, including an imaging beam generator which is adapted to transmit an imaging beam through the eyepiece, whereby the person's eye reflects a light beam back to the scanning module.

4. The eyepiece of claim 3, wherein the imaging beam generator produces an infrared optical imaging beam.

5. The eyepiece of claim 1, wherein the eyepiece and lens is customized for any astigmatism and aberrations of the person.

6. The eyepiece of claim 1, including a right and left eyepiece for each of the right and left eyes of the person.

7. The eyepiece of claim 1, wherein the eyepiece comprises right and left detachable eyecups each with an index and adapted to mate with a respective right and left eyepiece body to provide mating of the correct right or left eyecups with the respective eyepiece body.

8. The eyepiece of claim 1, further including a MEMs scanning module.

9. The eyepiece of claim 1, wherein the lens is a variable lens.

10. The eyepiece of claim 1, wherein the lens is a phoropter trial lens set.

11. The eyepiece of claim 1, wherein the eyepiece contains an RFID chip to uniquely identify the person for whom the eyepiece is customized, and parameters for customization.

12. The eyepiece of claim 1, wherein the eyepiece includes at least one filter.

13. The eyepiece of claim 1, wherein the eyepiece includes a lens optimized for imaging different areas of the retina of the person.

14. The eyepiece of claim 1, including a fundus imaging device.

15. The eyepiece of claim 1, including an eye measurement device.

16. The eyepiece of claim 1, wherein the eyepiece includes an eyecup for performing a dry eye test.

17. The eyepiece of claim 1, wherein the eyepiece includes a customized eyecup having an electrical sensor for performing multifocal electrophysiology exams.

18. The eyepiece of claim 1, wherein the eyepiece includes a light source to illuminate an eye.

19. An eyepiece for use in a system for obtaining data of the optical system of a person, comprising:
an eyepiece customized to contact and tightly fill in a person's eye socket and having a refractive lens manufactured to be customized to match a person's eye refraction characteristics, wherein the eyepiece abuts the person's eye socket and an imaging system and sets the correct refraction and optical path length between the person's eye and imaging system so that the retina is at the correct distance from the imaging system for the person;
a condensing system for receiving light from the refractive lens and condensing the light;
a mirror for receiving condensed light from the condensing system;
a retroreflector for receiving light from the mirror; and
an adjustable arm connected to the eyepiece and retroreflector for adjusting the position of the retroreflector relative to the eyepiece.

20. The eyepiece of claim 19, including a right and left eyepiece for each of the right and left eyes of the person.

21. The eyepiece of claim 19, wherein the eyepiece comprises right and left detachable eyecups each with an index and adapted to mate with a respective right and left eyepiece body to provide mating of the correct right or left eyecups with the respective eyepiece body.

22. The eyepiece of claim 19, wherein the lens is a variable lens.

23. The eyepiece of claim 19, wherein the lens is a phoropter trial lens set.

24. The eyepiece of claim 19, wherein the eyepiece contains an RFID chip to uniquely identify the person for whom the eyepiece is customized, and parameters for customization.

25. The eyepiece of claim 19, wherein the eyepiece includes at least one filter.

26. The eyepiece of claim 19, wherein the eyepiece includes a lens optimized for imaging different areas of the retina of the person.

27. The eyepiece of claim 19, including a fundus imaging device.

28. The eyepiece of claim 19, including an eye measurement device.

29. The eyepiece of claim 19, wherein the eyepiece includes an eyecup for performing a dry eye test.

30. The eyepiece of claim 19, wherein the eyepiece includes a customized eyecup having an electrical sensor for performing multifocal electrophysiology exams.

31. The eyepiece of claim 19, wherein the eyepiece includes a light source to illuminate an eye.

* * * * *